United States Patent [19]

Hudson et al.

[11] Patent Number: 5,679,539

[45] Date of Patent: Oct. 21, 1997

[54] OXIDIZED POLYETHYLENE OR POLYPROPYLENE PARTICULATE SUPPORTS

[76] Inventors: Derek Hudson, 52 El Cerrito Ave., San Anselmo, Calif. 94960; Ronald M. Cook, 7 Meadow La., Novato, Calif. 94947

[21] Appl. No.: 377,808

[22] Filed: Jan. 24, 1995

[51] Int. Cl.$^6$ .......................... C12P 21/06; C12N 11/06; G01N 33/549; C07K 17/06

[52] U.S. Cl. .................. 435/68.1; 435/41; 435/91.1; 435/101; 435/180; 435/181; 435/240.23; 435/240.24; 436/531; 436/532; 530/412; 530/415; 530/417; 530/815; 530/816; 530/402; 525/383

[58] Field of Search ........................... 435/815, 174, 435/177, 176, 180, 181, 182, 41, 68.1, 91.1, 101, 240.23, 240.24; 436/531, 532; 530/412, 415, 417, 815, 816, 402; 525/383

[56] References Cited

U.S. PATENT DOCUMENTS

| | | | |
|---|---|---|---|
| 4,177,253 | 12/1979 | Davies et al. | 424/1 |
| 4,256,840 | 3/1981 | Meitzner et al. | 521/33 |
| 4,351,909 | 9/1982 | Stevens et al. | 521/28 |
| 4,501,826 | 2/1985 | Meitzner et al. | 521/29 |
| 5,174,996 | 12/1992 | Frankfurt et al. | 424/401 |
| 5,321,094 | 6/1994 | McGee | 525/387 |
| 5,576,220 | 11/1996 | Hudson et al. | 436/518 |
| 5,585,275 | 12/1996 | Hudson et al. | 436/518 |

FOREIGN PATENT DOCUMENTS

| | | |
|---|---|---|
| 49-025086 | 3/1974 | Japan . |
| 51-029558 | 8/1976 | Japan . |
| 90265526 | 10/1992 | Japan . |
| 04335035 | 11/1992 | Japan . |

OTHER PUBLICATIONS

K.K. Unger and R. Janzen, *J. Chromatography*, 373, 227–264 (1986).

"Solid Phase Biochemistry, Analytical and Synthetic Aspects", Ed W.H. Scouten, John Wiley, NY, 1983.

Oligonucleotide Synthesis, A Practical Approach, Ed. by M.J. Gait; IRL Press, Oxford, 1984, pp. 35–51 & 81.

G. Jung, A.G. Beck–Singer, *Angew. Chem. Int. Ed. Eng.* 31, 367 (1992).

G. Barany and R.B. Merrifield in The Peptides, Analysis, Synthesis, Biology, vol. 2A; Ed. E. Gross and J. Meienhofer, Academic Press, NY, 1980 pp. 3–35.

J.R. Hollahan, B.B. Stafford, R.D. Falb and S.T. Payne, *J. App. Polymer Sci* 13, 807 (1969).

S.R. Holmes–Farley, Robert H. Reamey, Thomas J. McCarthy, John Deutch, and G.M. Whitesides, *Langmuir* 1, 725–740 (1985).

S.S. Bentjen, D.A. Nelson, B.J. Tarasevich and P.C. Rieke, *J. App. Polymer Sci.* 44, 965 (1992).

N.R. Shenoy, J.M. Bailey and J.E. Shively, *Protein Science* 1, 58 (1992).

H.M. Geysen, R.H. Meleon and S.J. Barteling, *Proc. Natl. Acad. Sci. USA* 81, 3998 (1984).

J. Vagner, V. Krchnak, N.P. Sepetov, P. Strop, K.S. Lam, G. Barany and M. Lebl in "Innovations and Perspectives in Solid Phase Synthesis; Proceedings of the IIIrd International Symposium", R. Epton, Ed., Mayflower, Birmingham, p. 347 (1994).

K.S. Lam, S.E. Salmon, E.M. Hersh, V.J. Hruby, W.M. Kasmierski and R.J. Knapp, *Nature* 54, 82 (1991).

S. Birnbaum, P–O Larsson and K. Mosbach in, "Solid Phase Biochemistry, Analytical and Synthetic Aspects", Ed W.H. Scouten, John Wiley, NY, 1983, chapter 15.

*Primary Examiner*—David M. Naff

[57] ABSTRACT

Polyolefin particles are chemically modified by oxidation to provide a large surface area and high loading. The particles result in low back pressure in column systems, and are economical to manufacture. The particles are useful as supports in a wide range of applications including general organic as well as biopolymer synthesis, library methods, purification processes and enzyme mediated processes. In a preferred embodiment, polyethylene or polypropylene particles are oxidized in a solution containing trifluoroacetic acid or trifluoromethane sulfonic acid, chromium trioxide and sulfuric acid to provide the particles with a chemically reactive irregular surface and open channels that extend below the surface and up to essentially the length of the radius of the particles resulting in increased surface area and decreased density. The particles have pendant functional groups produced by the oxidation and/or by subsequent chemical reaction. The pendant functional groups may be attached to spacer arms that are attached to the surface of the particles. Biological material such as proteins, enzymes and whole cells may be immobilized on the particles.

19 Claims, 1 Drawing Sheet

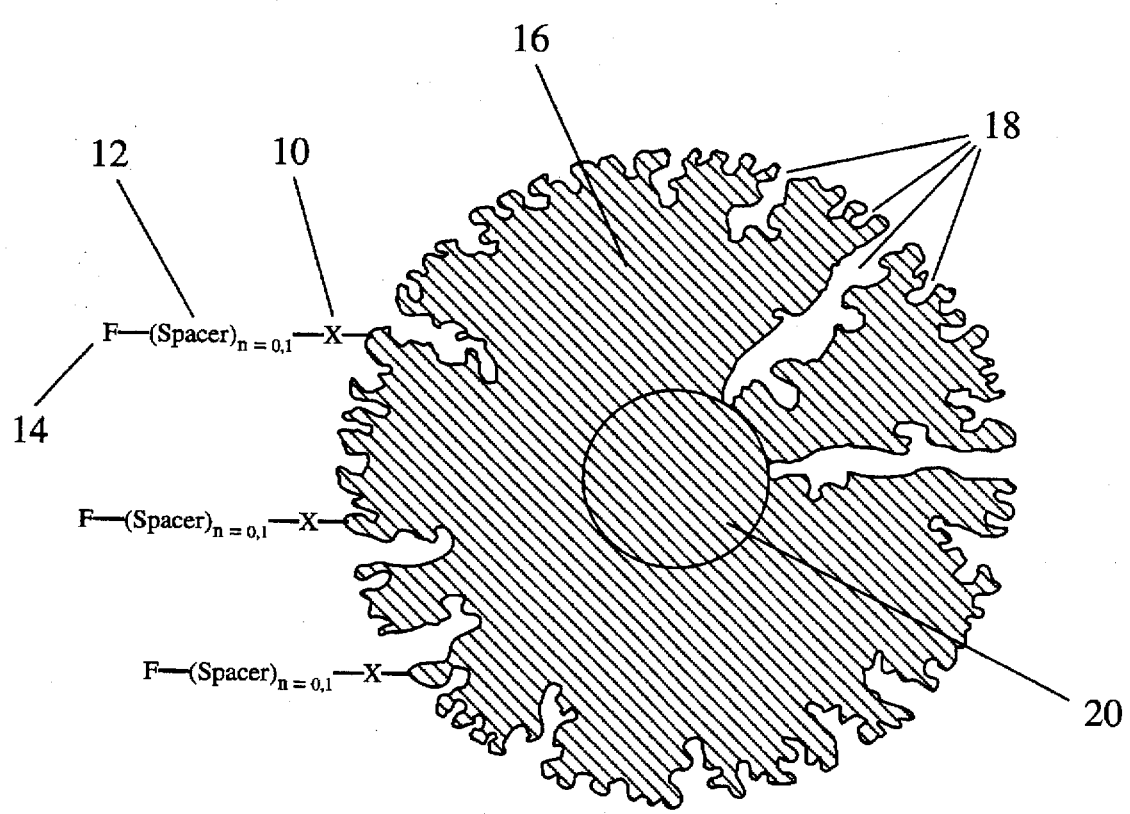

OXIDIZED POLYETHYLENE OR POLYPROPYLENE PARTICULATE SUPPORTS

FIELD OF THE INVENTION

Particulate materials are widely used for the synthesis, purification and analysis of all molecules.

PRIOR ART

Listed are noteworthy examples of particulate materials (with preferred applications given) which are of use for synthesis, purification and analysis:

i) Highly cross-linked macroreticular polystyrenes (ion-exchange processes, DNA synthesis). Such rigid materials are incompatible with some solvents, and are chemically reactive. Synthesis applications are limited.

ii) Low cross-linked organic swellable polystyrenes (peptide synthesis). Used for over 30 years in the Merrifield method of solid-phase peptide synthesis, these materials swell and shrink to variable amounts depending on the solvent and substitution, and are unsuitable for DNA synthesis, flow and column processes, many chemical processes, or any aqueous systems.

iii) Silicas (HPLC supports). Useful only in chromatographic applications, and very fine particle sizes pumped at high pressures are required.

iv) Controlled pore glass (DNA synthesis, enzyme immobilization). These materials have provided the support of choice, to date, for small scale DNA synthesis. Nevertheless, because of the fact that synthesis occurs within defined pores, physical restraints limit both the size of target accessible and the loading. In addition CPG is unstable to a range of different chemistries, and the particles are fragile and easily degraded by mechanical agitation and high pressures. The particles are exceedingly irregular in size distribution and shape, and consequently are unsuitable either for chromatography or bead based library methods.

v) Cross linked polysaccharides and polyacrylamides (affinity, ion-exchange and size exclusion chromatography). These materials are only compatible with aqueous systems (and are unsuitable for synthesis), and are subject to bacterial degradation and contamination with endotoxins.

vi) Graft copolymers of polyethylene glycol and low cross-linked polystyrene (organic synthesis, peptide synthesis, bead based library methods). These materials (Tentagel, Rapp Polymer; PEG-PS, Perceptive Biosystems) are considerable improvements over the unmodified parent polymers (ii above) being compatible with column reactors and a wider range of solvents. Their compatibility with aqueous systems is very poor, and typically less than 1% of functional groups supported on these materials are accessible in water.

The problems of obtaining equilibration with materials entrapped within the pores of gel-phase swellable polymers have long been recognized. In synthesis applications these supports also give rise to dilution of activated species (reducing reaction rates), raising volumes of solvents and reagents required, and slowing processes due to the need for lengthy equilibration as solvents and reagents diffuse into the beads. In chromatographic applications there is a concomitant increase in volume of elution buffer required, and increase in chromatography time due to slow equilibration.

For this reason high surface area, yet rigid, polymers have real advantages. In ion-exchange chromatography, macroreticular polystyrenes possess advantageous properties [Meitzner and Olin, U.S. Pat. 4,5501,826 (1985); Meitzner and Olin, U.S. Pat. No. 4,256,840 (1981)], as do composites of very fine particles absorbed onto the surface of larger carriers [Stevens and Rich, U.S. Pat. No. 4,3351,909 (182)]. Pellicularly functionalized silicas briefly enjoyed success for HPLC but the popularity has waned due to stability problems. For a variety of affinity applications latex microspheres, particularly those bearing internally deposited paramagnetic materials, have become increasingly popular. The application of particulates for chromatography is discussed by Unger and Janzen [J. Chromatography, 373, 227 (1986)]. The application of particulates for affinity separations is discussed in "Solid-Phase Biochemistry, Analytical and Synthetic Aspects", Ed. by W. H. Scouten. The application of particulates for immobilized enzymes is discussed in Methods in Enzymology, Volume XLIV, Ed. K. Mosbach. The application of particulates for nucleotide synthesis is discussed in "Oligonucleotide Synthesis, A Practical Approach, Ed. by M. J. Gait". The application of particulates for organic synthesis is reviewed in "Benchmark Papers in Organic Chemistry, Vol 2. Solid-Phase Synthesis,Eds. E. C. Blossey and D.C. Neckers". The application of particulates for library applications is reviewed by Jung and Beck-Singer [Angew. Che. Int. Ed., Eng. 31, 367 (1992)], and the application of particulates for peptide synthesis is reviewed by Barany and Merrifield in "The Peptides, Analysis, Synthesis and Biology, Vol 2A, Ed. E. Gross and J. Meienhofer", 1980.

Both gas phase plasma amination [J. R. Hollahan et al., J. App. Polymer Sci, 13, 807 (1969)] and solution phase oxidation [e.g. Holmes-Farley et al., Langmuir, 1, 725 (1985); S. S. Bentjen et al., J. App. polymer Sci, 44, 965 (1992)] have been used to modify polyolefin surfaces and films, and the products have been used in a variety of applications, including synthetic papers [Mitsubishi Co., Japanese Patent 76029558], and sequencing of immobilized peptides [N. R. Shemoy et al., Protein Science 1, 58 (1992)]. A useful modification has been surface functionalization of polyolefin pins by gamma-ray induced grafting of acrylic acid [H. Mario Geysen et al., Proc. Natl. Acad. Sci. U.S.A, 81, 3998 (1984)]. A variety of methods have been used to prepare surface oxidised and otherwise modified polyolefin particles [e.g. McGee, U.S. Pat. 5,321,094 (1994)], but these have only been used in formulations for toners and inks [Mitsui Petrochem, Japanenese Pat. 90265526 (1992)], nail enamels [C. Frankfurt et al., U.S. Pat. 517,496 (1992)], manufacture of moldings [Misui Petrochem, Japanese Patent 4335035 (1992)], ski coatings and other applications unrelated to molecular synthesis, analysis, or display. This prior art does not teach the preparation or the usefulness of high surface area particles created by aggressive chemical modification of polyolefin particles.

OBJECTS AND ADVANTAGES OF THE INVENTION

It is the principal object of the invention to provide polyolefin particles, modified by the process of chemical invection, for molecular synthesis, analysis, separation and recognition. The structure of the functionalized Chemically invected PolyOlefins (CPO's) confers manifest merits. The matrix is rigid, chemically inert and robust (both mechanically and chemically); and its functionalization is accessible, and highly chemically reactive. CPO particles are easily prepared in a range of substitution levels from economical and generally available polyolefins.

The prior art, reviewed above, shows that although existing particulate materials are available for specific applications within the field of the invention, none is of general applicability or bear any resemblance to chemically invected polyolefin particles. Accordingly several objects and advantages of the invention are listed below. The discussion explores a variety of applications of CPO's; this list is illustrative and not restrictive, and could be expanded by any one knowledgeable in the art.

CPO's in Enzyme Mediated Processes

An important attribute of CPO's is that they are totally compatible with aqueous media, and show a surprising lack of steric inhibition to interaction with protein molecules. Enzyme mediated processes, such as hydrolysis, phosphorylation, ligation or the polymerase chain reaction, can be performed directly on a substrate assembled on the materials. In quantitative studies (Experimental) trypsin and chymotyrypsin digest, in a single treatment, over 50% of total CPO bound peptides. These experiments provide an important paradigm for the improvements provided in biorecognition processes involving CPO bound entities. Studies by Vagner et al. [in "Innovation and Perspectives in Solid-Phase Synthesis and Related Technologies, R. Epton Ed., 1994] showed, under similar conditions, less than 1% cleavage with peptides assembled on a commercial polethyleneglycolpolystyrene graft copolymer, Tentagel (widely used in bead based library methods). CPO's, therefore, have clear advantages for not only bead-based library applications, but also affinity chromatography and enzyme mediated reactions. Since accessibility to enzyme reaction and chemical reactivity are directly correlated, then the process described of enzyme clipping, provides an economical method applicable on very large scales to select, extremely beneficially, only the most reactive and accessible sites. In a related application (see below) enzymes maintain high activity when immobilized on CPO's.

CPO's in "bead" based library methods

The recent introduction of library methods promises to revolutionize pharmaceutical development. In the bead based process [K. S. Lam et al., Nature, 54, 82 (1993)] then all possible combinations of molecules constructed from cycles of monomer addition are prepared by divide, couple and recombine methods (DCR), in which an initial lot of beads is aliquoted into separate sub-lots for the addition of individual monomers; then the resin is recombined and mixed during subsequent deprotection of a temporary protecting group. Repetition of this process for as long as required gives rise to all possible combinations. An absolute limitation is provided by the complexity, however; with 20 subsets and 6 addition cycles there are 64 million possible combinations. With a 90 micron CPO containing about $7 \times 10^6$ particles per gram, 20 grams of support provides adequate redundancy, assuring that virtually all possibilities are present.

CPO's provide significant improvements in that:

i) The appended moieties are displayed in highly accessible manner. This attribute ensures rapid and efficient equilibration with aqueous solutions of the target acceptors (receptors, Mabs, etc.). It should be emphasized that unmodified polyolefin particles are highly hydrophobic and entirely unwetted by aqueous systems. In normal polystyrene based bead systems, such as with the graft copolymer Tentagel used by Selectide (Tucson, Ariz.), only about 1% of the displayed peptide can interact with the target protein. With CPO's efficient interaction is permitted, increasing sensitivity (or correspondingly reducing dramatically the amount of expensive highly purified labeled recombinant target required for assay). The wash volumes required to remove unbound molecules are also reduced.

ii) CPO's ensure a higher local concentration of displayed molecules compared to that obtained for peptides uniformly distributed throughout the entire bulk of a gel polymer bead. If prepared by DCR strategies then these are all identical. Since most targets have multiple binding sites (e.g. Mab's, cytokine receptors) then multivalent binding will occur giving rise to much stronger interactions. This is important as it facilitates the identification of low affinity binding interactions, and may assist attempts to find agonists for receptors which are activated by dimerization (e.g. human growth hormone).

iii). General usefulness. The chemical inertness and unswollen nature of the material makes it ideal for "organic diversity" libraries, where alternative solvents and more drastic conditions are required. High reactivity is even more essential for reactions which proceed slowly even in solution, and the accessible distribution obtained in CPO particles gives reactivity close to that obtained in solution, and considerably better than that with conventional cross-linked gel polymers where diffusion can be rate limiting.

iv). Suitability for proportioning. A deficiency of many materials is their poor mechanical stability, and their high specific density, which make them unsuitable for automatic proportioning. A noteworthy example is CPG. The low density of CPO particles, and their physical strength, are ideal. One CPO (derived from high density polyethylene) has close to neutral buoyancy in neat DMF, as well as in a 60% water/40% methanol mixture. In DCR methods suspension in DMF and proportioning via syringe is highly effective. Distribution for assay purposes of product bead libraries in the methanol/water cocktail also facilitates assays.

v) Fluorescent Detection. Traditional polystyrene bead based library methods are incompatible with fluorescence detection since the highly aromatic nature of the polymer provides intrinsic fluorescence and also quenches the signal. CPO materials are transparent, and provide no intrinsic fluorescence background. Used along with the sensitive ELF substrate (Molecular Probes, Oregon), and alkaline phosphate conjugates, sensitivity of detection is enhanced dramatically. A further, significant advance is the application of fluorescence based automated cell sorters for isolation of positive beads rather than traditional manual removal with forceps under the microscope.

vi) Novel HRP, or alkaline phosphatase conjugate or radio-labeling assay technology. A further merit is that the DCR method can be applied in an entirely different manner than in the normal bead staining method. A small particle size CPO library could be subjected to the DCR technique, deprotected, placed in a column, incubated with buffered receptor-enzyme conjugate, and unbound conjugate removed by washing. The particles are suspended in cocktail and aliquoted into a 20×20 well plate using a repipettor. The substrate is added to each well with assay buffer. Formation of color or fluorescence in any well indicates binding. In this assay/amplification technique high sensitivity is obtained with long reaction; and it is unnecessary to look for individual stained beads. The 370,000 particles in the strongest well are then reproportioned, fresh substrate added and again a selection made. The 924 particles are then be finally proportioned, and the structures determined. Note this final distribution gives 2 particles per well on average. These can be sequenced together or placed on a grid and mass spectroscopy used (the SIMS-TOF method). Alternatively the technique can be used with high specific activity radiolabeled receptors using wells with a thin Saran wrap base and autoradiography for detection of productive binding.

A key question is the amount of displayed library component per particle. Since a typical 90 micron CPO is estimated to contain ca. $6 \times 10^6$ particles/g, and there are $64 \times 10^6$ possible combinations in a linear hexapeptide library, use of 20 g of the material ensures that, in this example, almost all possible combinations are present. With smaller particle sizes there is a dramatic reduction in the amount of material needed to perform a complete probe compared with that required with conventional beaded supports. With a loading of 60 µmol/g, then each 90 micron particle will display 10 picomole of a single component of the library. This is quite sufficient for Edman sequence analysis; however, 1 picomole of material can be readily sequenced by the SIMS-TOF mass spec. analysis system, giving the potential to miniaturize the system even further.

CPO's in biomolecule assembly:

In many ways the properties of CPO's parallel those of controlled pore glass (CPG) as regards usefulness for biomolecule assembly. The relative chemical inertness and uniformity of pore size distribution of CPG have been the prime attributes which have resulted in its pre-eminent position as the support of choice for DNA, RNA, PNA and peptide/DNA hybrid synthesis. The relative expense, mechanical fragility and lability to extremes of acidic and basic conditions have limited application to peptide synthesis. Unlike CPG, CPO's are stable to great extremes of reaction conditions (even to liquid HF used for side-chain deprotection and cleavage in the conventional Merrifield method). Their efficacy results not from a uniform porosity, but from surface connected "pores" which result, effectively, in an enormously augmented surface area. The defined porous nature of CPG imposes a size limitation on the target oligomer, it being generally accepted that CPG with 500 Å pores is unsuitable for the synthesis of oligonucleotides of greater than 50 residues. No such size limitations are involved for syntheses on the augmented surfaces of CPO particles.

During synthesis operations excess reagent and wash solvent can be removed by gas blow out protocols, minimizing wash solvent usage and dilution effects in subsequent reactions. The resultant economy and efficiency is especially important in large-scale applications.

During biomolecule assembly on CPO particles, the physical separation imposed on the moieties under construction by the augmented surface suppresses intermolecular aggregation effects. Such aggregation provides one of the most severe limitations to the use of low cross-linked polystyrene beads. With the latter support during peptide synthesis interpeptide hydrogen bonding results in restricted access to amino groups and diminishes reaction rates.

The Examples demonstrate the high efficiency of CPO particles in both peptide and nucleic acid synthesis applications.

CPO's in chromatographic applications:

CPO's are highly suitable for the separation of biomolecules. The drastic chemical processing ensures that the supports are free of bacterial contaminants and cannot release endotoxins. They may be autoclaved, or treated with sterilizing solutions without change in their separation characteristics. Their structure makes them totally resistant to enzymatic or chemical degradation, and should confer virtually indefinite reusability. Total compatibility with aqueous media and high flow rates produces rapid separations in non-denaturing conditions. The totally solvent accessible augmented surface results in ultra rapid equilibration reducing both separation times and buffer requirements. The chemical inertness of CPO's ensure that highly acidic to highly basic conditions can be used with no deleterious effects; such conditions rapidly degrade HPLC silicas.

Because of the economy of the support and lack of back pressure, >20 micron CPO's are ideally suited for large scale applications. Materials are acid/base stable and can be recycled without detectable change in efficiency. For ion exchange applications they have been prepared with incorporation of acid carboxylic and sulfonic acid functions for cation exchange processes and chromatography, as well as with basic groups (primary, secondary, tertiary and quaternary amines) for anion exchange processes.

Total compatibility with all solvents from water to paraffin's without change of dimensions, flow rate, or back-pressure ensures their suitability for normal and reverse phase applications. A variety of hydrocarbon (preferably 3 to 30 carbon atoms) and aromatic (preferably 1 to 3 rings) functionalized materials have been used in reverse-phase separations of nucleotides and proteins. The weakly hydrophobic nature of hydroxyl functionalized CPO's make them highly useful for biomolecule separation without further derivatization.

The ease with which biomolecules can be assembled on CPO's makes then ideal for affinity supports in which the displayed ligands may either be immobilized onto the CPO's, or directly synthesized thereon.

CPO's in organic synthesis applications

Solid-phase supported organic synthesis is an area of tremendous importance to the routine automation of chemical processing. It is especially applicable to pharmaceutical development, wherein the rapid preparation of related molecules expedites the development of potential drug candidates. The method may be divided into two classes: i) those in which the reagents are immobilized and these perform reactions on solution phase substrates, and ii) those in which the substrates are immobilized and solution chemical reactions are performed on them. Both variations offer the key advantages of simple manipulations and automation, combined with the ability to use large excesses of reagents (thereby ensuring complete reaction) which are simply removed by filtration or washing.

To date, the vast majority of organic syntheses performed on or with solid-phases, have used polystyrene supports; although occasionally CPG, silica and polyacrylamide coated plastics have been applied. CPO materials offer tremendous advantages: they do not shrink or swell and are compatible with a wide solvent range, from highly polar to very non polar; are thermally, chemically and mechanically stable, and provide ease of monitoring. Their rigidity permits their use for gas-phase reactions with volatile reagents, a process anticipated to be one of the most important applications of CPO's. Gas-phase reactions are exceedingly economic; no solvents or washes are required; they may be performed at extremes of temperature (or pressure) without problem. Facile monitoring of reactions on CPO's (especially CPE) is possible since they are transparent in NMR and IR spectroscopic ranges where aromatics, olefin, carbonyls and a host of other groups can be determined. In contrast to these favorable attributes of CPO's, then polystyrenes shrink and swell, and cannot be used in many common solvents. Additionally, in contrast with CPO's, they are highly chemically reactive, so that a range of reactions, such as nitration's, aromatic substitutions, Friedel Crafts reactions, and vigorous oxidation's or reductions are prohibited. Spectroscopic monitoring of polystyrene supports is frequently masked in the IR and NMR by the polymer absorption.

CPO's for protein, enzyme and cell immobilization

The use of immobilized enzymes for a variety of pharmaceutical and industrial processes is becoming more and more important. Two well proven examples are the production of 6-aminopenicillanic acid by Sephadex immobilized E. Coli produced penicillin acylase, and the use of glucose isomerase in the production of high fructose corn syrup. Commercially available supports compatible with column processing include PEI impregnated alumina (UOP), controlled pore glasses (e.g. 300 Å macroporous silica from Baker, agarose beads (Biorad), Sepharoses (Pharmacia), microporous membranes [nylon (Pall), PVDF (Millipore) and cellulose/acrylic (CUNUO], high porosity 5% cross linked polystyrenes (National Starch) . Data (Examples) show that the enzyme trypsin retains high activity when immobilized on CPO. These materials provide close to neutral buoyancy and can be used in very large scale batch reactor processes or in column reactors equally efficiently; they are not subject to degradation by microbial contamination. Above all, the extreme economy of these materials, and their longevity make them ideally suited for industrial processes. Enzymes immobilized on CPO's have potential for hydrolysis or formation of peptide, oligonucleotide and oligosaccharide bonds, as well as in a host of different applications including phosphorylation, deacylation, ligation and isomerization. A fascinating application is to the polymerase chain reaction using non-thermally stable but highly efficient enzymes. The immobilized polymerase may then simply be separated from the reaction (e.g.. by centrifugation, filtration or magnetization), the chains denatured by heating, then recombined with the enzyme for further amplification. This modification eliminates the need for the enzyme to be thermally stable, and may reduce the incidence of errors.

Further application is envisioned in the field of cell immobilization [reviewed by S. Birnbaum et al.,in "Solid-Phase Biochemistry, Analytical and Synthetic Aspects", Chapter 15; Ed. by W. H. Scouten]. The most vital consideration is for the support bound cell to remain viable. Physical or chemical adsorption onto the surface of a CPO particle will provide a highly compatible environment.

Further exceptional usefulness is found in protein functionalized CPO's, especially CPO's with magnetic cores prepared by melt processes. Immobilization of streptavidin on such magnetic CPO's allows biotinylated oligonucleotides to be immobilized; and these particles can then be used to isolate specific RNA or DNA sequences, and a whole host of biotechnology applications. In related applications concanavalin can be immobilized and used for the affinity purification of specific glycoproteins.

BRIEF DESCRIPTION OF THE DRAWING

The FIGURE depicts a cross section of typical CPO particles containing functional groups and spacers.

SUMMARY OF THE INVENTION

This patent describes the unexpected and beneficial properties provided by polyolefin particles (POP's) that have been modified by physical and chemical treatments to provide high surface area controlled materials suitable for molecular synthesis, analysis, separation and recognition. Although other particulate materials have specific areas of applications, no other material is so generally useful. The aggressive oxidative treatment of POP surfaces employed is termed chemical invection. This process allows controlled tailoring of polyolefin particles from surface functionality only (pellicular forms), through increasingly more invected, highly accessible and highly loaded variations, to lower density, ultra high load variations. These materials prepared from polyolefin particles by controlled processing are named CPO's (CPE, a particularly useful selection, is controlled polyethylene derived from PEP, polyethylene particles). Important variations are provided by two component melt processing. This enables the incorporation of paramagnetic materials as well as of similar or dissimilar polymers within the melt, and within particles produced by milling. Chemically invected versions are then prepared after dissolution of accessible foreign incorporates. Use of CPO materials in synthesis applications allows reactions to be performed in as concentrated solution as possible (raising reaction rates), diminishes the volumes of reagents and solvents required, and speeds washing and reactions in general due to the rapid equilibration achieved. In analytical and bulk chromatography applications the ultra-rapid equilibration provided by surface display leads to high resolution and fast cycle times.

DESCRIPTION OF THE INVENTION

Our initial studies showed that DNA could be prepared with standard automated synthesis protocols on a whole range of chemically functionalized Poly Olefin Particles (POPs). Plasma amination gave very low levels of substitution (<200 nmol/g), and poor quality products (unless long spacer arms were employed). Aqueous oxidation of PE particles with. chromic acid at 56° C., followed by BOP mediated coupling of 1,13-diamino-4,7,10-trioxaundecane, $NaBH_4$ reduction (to reduce undesired keto or aldehyde functions) and standard nucleoside functionalization gave loading close to 4 μmoles/g. Modest increase in level of functionalization resulted from extending the reaction, elevating the temperature, or using excess oxidizing reagent. Both peptide and DNA syntheses occurred efficiently on appropriately linked material. Remarkably, repeated oxidation at somewhat more elevated temperatures in the presence of large amounts of inert halo acids (e.g. trifluoroacetic acid or trifluoromethanesulfonic acid) resulted in particles of unchanged dimensions, but decreased density, which have highly modified surfaces, and capable of being substituted at over 150 μmol/g (an improvement by 3 orders of magnitude over plasma amination). In addition, the products provided excellent coupling efficiency in biopolymer synthesis with a simple spacer arm. Variation in the reaction conditions allowed control of the invection and functionalization.

The derivatized CPO particle, as depicted in the FIGURE, bears chemical functional groups, X (10). These may be carboxyl, keto, aldehyde, hydroxyl or the like (or mixtures) depending on the nature of the polymer. Group X may, alternatively, be transformed into a variety of other functions by chemical reaction, and then further modified (including keto, aldehyde and carboxylic groups introduced by oxidation procedures, transformed by coupling with amines to give amides, reduction to hydroxyls, or by reductive amination to secondary amines, for example). In the FIGURE, X (10) represents the surface substituent introduced, either directly from chemical functionalization or by transformation of the initially introduced group. A spacer (12) between X and the desired functionality F (14) is optional, and can be omitted entirely (12, n=0). In general, though, spacer (12) is exceedingly useful. In biochromatography, and library methods it allows biological molecules to approach the support without steric effects. A similar effect occurs in synthesis applications in which steric effects reduce reaction rates in the absence of appropriate spacers. The spacer may be a simple bifunctional molecule permitting reaction with X (10), and subsequent attachment of F (14). It may bear F already incorporated. It is frequently useful for the spacer to be polyfunctional, as with polyethylene imine, polyallylamine, polylysine, and saccharides such as substituted dextrans. F (14) may represent an added hapten for chromatography, e.g. a simple linear hydrocarbon for reverse-phase chromatography or a tertiary amine for anion exchange chromatography, an immobilized chemical reagent, an enzyme, or be an attached or constructed biopolymer, such as a peptide, protein or oligonucleotide for affinity purification, analysis or in diagnostic applications. It may also represent a cleavable or non-cleavable handle for chemically and/or enzymatically mediated biopolymer assembly, or, in certain chromatographic applications, may advantageously be eliminated.

The chemistry used in modifying, or chemically invecting, the surface produces a layer 16 of variable thickness depending on the severity of the reaction conditions. The ability to tailor this variable according to the individual application is important; for preparative synthetic applications a thicker layer gives rise to a higher loading. Mild oxidation gives rise to predominant surface modification, whereas oxidation in the presence of large concentrations of halo substituted acids (trifluoroacetic acid, trifluoromethane sulfonic acid and the like), gives rise to chemical invection (penetration and erosion of the surface leading to lower density high surface area particles). The extent of chemical invection can be controlled closely by adjustment of conditions; normally by modifying the excess of reagents, the processing time and/or the temperature.

There is no true dividing line between lightly chemically invected relatively low surface area pellicular CPO particles, with shallow surface functionalization, CPO's in which channels have been induced in relatively thin layers, or, ultimately, in which channels and branch channels have been produced in depths up to the total radius of the particle with concomitant enormous increase in surface area. A variety of chemically inert polyolefins are suitable. These include polyethylene, polypropylene, polyhalogenated olefins, polymethylpentene, etc. Polyethylene, and polypropylene are preferred materials since they provide the required general inertness, can be readily chemically invected, and are available in bulk as defined range particles at very economical rates (compared to alternative materials).

Materials consisting of conglomerates of CPO particles are highly useful, as are variations incorporating foreign materials, especially paramagnetic or magnetic particles. These can be prepared by melting or forming the polyolefin stock, suspending in the melt the material to be incorporated and converting this blend into particulate form.

PREFERRED EMBODIMENTS OF THE INVENTION

The following detailed description illustrates the invention by way of example, not by way of limitation of the principles of the invention. This description will clearly enable one skilled in the art to make and use the invention, and describes several embodiments, adaptations, variations and uses of the invention, including what we presently believe is the best mode of carrying out the invention.

The particle may be spherical (as represented in the FIGURE), or may be of any other suitable regular or irregular shape. The particle size distribution may be over a considerable range. Particle size may vary from sub-micron sizes to 2000 microns. Smaller particles are preferred for HPLC applications (1–20 microns, EXAMPLE 6), medium size particles for synthesis applications (20–100 microns), and large particles (50 to 200 microns) for applications in which particles need to be handled individually (library methods). For synthesis a preferred particle size is 90 microns. Preferred spacers (FIGURE) are from unmodified or terminally substituted polyethylene glycol's; diamino substitution, as with 3,6,9-trioxatridecane-1-13 diamine or Jeffamine ED-600 (both from Fluka), conveniently introduces amine functionality and spacer arm simultaneously (Example 1, 4). It is preferred also in this method, Example 4, to reduce any aldehyde and keto functions formed during oxidation with sodium borohydride.

For synthesis applications highly invected polyolefin particles are preferred (Example 3), whereas for enzyme immobilization, affinity purification and some chromatographic applications more lightly loaded variations are preferred (Examples 1,2 and 5). The preferred source for unmodified polyethylene particles is Shamrock Technologies (Newark, N.J.), and polypropylene is from Himont (Wilmington, Del.) but requires milling (as in Example 1).

EXAMPLE 1

Preparation of surface functionalized polypropylene particles

High density polypropylene (ex Himont, Wilmington, Del., particle size 100–500 microns, 5 g) was coarsely ground (4×15 seconds in a standard laboratory IKA grinder, supplied by Tekmar, Ohio), and was oxidized with potassium dichromate (10 g) in 40 mL of 1:1 c. $H_2SO_4$ for 5 minutes at 75° C. The reaction was diluted with water, filtered, and the product washed repeatedly with water, then methanol and dried. A sample (1 g) was treated under anhydrous conditions with thionyl chloride (2.5 mL). After 30 minutes the mixture was filtered and the particles washed with dry ether, the immediately added to 3,6,9-trioxatridecane-1–13 diamine (2.5g) in dichloromethane (2.5 mL). The reaction was shaken overnight, then washed with DCM, DMF, DMF/water, water and methanol, then dried. This aminofunctionalized form has been used in a variety of applications; when functionalized with DMT-T-succinate by standard protocols it gives a support loaded at 0.2 μmol/g which functions for DNA synthesis by standard amidite protocols less efficiently than does CPG.

EXAMPLE 2

Preparation of surface functionalized polypropylene particles by plasma amination.

An identical sample of polypropylene powder was plasma aminated in a thin film on a clean watch glass for 30 minutes with a nitrogen/hydrogen mixture in equipment manufactured by Surface Science Laboratories, Palo Alto. The powder was redistributed and reaminated for a further 30 minutes. This amino functionalized form was directly loaded with DMT-T-succinate and tested as described in Example 1 above to give an identical loading and synthesis efficiency.

EXAMPLE 3

Preparation of high loaded CPO from polypropylene particles

Polypropylene powder (Shamrock, Newark, N.J.; 200–300 micron, 10 g) was suspended in TFA (14 mL), water (20 mL) and sulfuric acid (8.5 mL). The reaction was stirred and heated in a water bath; when the temperature had reached ca. 65° C., chromium trioxide (6.5 g) was added. After a further 30 minutes gradually heating to 80° C. an additional equal aliquot of chromium trioxide was added. After a further 30 minutes, sulfuric acid (7.5 mL) and more chromium trioxide (13 g) were added and the reaction stirred for a further hour at 85° C. Finally more sulfuric acid (7.5 mL), water (20 mL). and chromium trioxide (13 g) were added, and left to react for 1 hour. Modification of these conditions, reducing or increasing the time, temperature, proportions or number of repeat treatments allowed the preparation of a whole range of materials with gradually increasing levels of substitution. The product from the described detailed procedure was isolated by diluting the reaction with water, and filtering the HOT mixture on coarse sintered glass. The CPO was then washed with water, 0.1M NaOH solution, water, 0.1M HCl, water until neutral, then methanol and dried. The product (7.5 g) had a loading of 90 µmol/g (determined by titration after subsequent functionalization). It has been modified into a variety of useful forms by subsequent chemical treatment; the following descriptions are illustrative of these, and not limiting.

a) Hydroxyl functionalized CPP. The total product from invection was suspended in THF under nitrogen and stirred gently as 2M lithium aluminum hydride solution in THF (10 mL) was slowly added by syringe. After cessation of effervescence, the reaction was heated to reflux for 1 hour, allowed to cool to room temperature and excess reducing agent removed by addition of ethyl acetate (5 mL). The reaction was filtered, and the particles washed repeatedly with 0.5M HCl, water and methanol.

b) Tosyl activated CPP. A sample of a) (1.2 g) was suspended in 1:1 acetonitrile/THF and treated overnight with 3 mL pyridine and p-toluenesulfonyl chloride (0.40 g). The suspension was filtered, washed with DMF, acetonitrile and dried.

c) Tertiary amine functionalized CPP. Tosyl activated CPP (total 1.2 g) was treated overnight with 10% piperidine in DMSO (5 mL). The suspension was filtered, washed with DMF (×3), methanol (×3) and dried. Titration showed 90 µmol/g tertiary amine functionalization

EXAMPLE 4

Preparation of high loaded amino functionalized CPE from polyethylene

55 Micron PEP (Shamrock, Newark, N.J.; 20 g) was placed in a 500 mL round bottom flask equipped with magnetic stirrer and reflux condenser and placed on a water bath. TFA (30 mL) was added and the mixture stirred whilst water (40 mL), and sulfuric acid (17 mL) were added. Finally chromium trioxide was added in portions. The water bath was allowed to warm. At 65° C., after 13 g of $CrO_3$ had been added, an exothermic reaction rapidly set in causing the reaction mixture to rise to 86° and to reflux. When the reaction had subsided a further 13 g of $CrO_3$ were added, and the reaction maintained at 86° C. for 1 hour. Further sulfuric acid (15 mL) was added with caution (!!), followed by more $CrO_3$ (26 g); the reaction was maintained at 86° C. for 1 further hour. At this junction all $CrO_3$ had been consumed, and the reaction was greeny black and v. viscous. A further 40 mL of water, 15 mL of TFA and 26 g of $CrO_3$ were added and reaction continued for 1 more hour with periodic mechanical assistance to stirring. The mixture was filtered hot on a sintered glass funnel, then the chemically invected particles washed with water until the effluent was colorless, then 2×0.1M NaOH, 2× with 0.1M HCl, water until washings were neutral, then methanol (3×). The total dried product was suspended in 1:1 acetonitrile/1,13 diamino-3, 6,9-trioxatridecane (60 mL), BOP (7.0 g) added and the reaction swirled overnight. The suspension was filtered, washed with DMF, dioxan/water (1:1, 2×); then treated with sodium borohydride (4 g) in 100 mL 1:1 dioxan/water for 1 hour on the sintered funnel. The suspension was filtered, and washed with water. These washes were isolated and subsequently carefully treated to decompose excess borohydride. The particles were then washed 0.1M HCl (2×), 0.1M NaOH (2×), water (until neutral), methanol (3×) and dried to give 15 g of product loaded at 110 µmol/g.

EXAMPLE 5

Preparation of Magneto CPE

Medium molecular weight polyethylene (4 g) was melted in a Pyrex container. Carbonyl iron particles (1.2 g) were mixed in with a glass rod to give a uniform melt. This was poured into rapidly stirred water (100 mL). The separated gray mass was milled for 4×15 seconds in a standard laboratory grinder (IKA, supplied by Tekmar, Ohio); microscopic evaluation shows ca. 50 to 100 micron particles containing internal specks of iron). The magnetic particulate material was treated with 1:1 methanol/2M HCl (20 mL) for 2 hours; then isolated by filtration and washed with water. The undried product was treated with potassium dichromate (5 g), water (10 mL) and sulfuric acid (10 mL) at 70° C. for 30 minutes with magnetic agitation. The hot suspension was filtered, washed with water (until effluent colorless), 0.1M NaOH, 0.1M HCl, water and methanol to give carboxyl functionalized magneto CPE (loading 10 µmol/g by titration).

EXAMPLE 6

Incorporation of Palmitic Acid to lightly invected PE

A stock solution of chromic acid was prepared (7.25 g chromium trioxide, in 10.5 mL water and c. $H_2SO_4$, 4 mL). High molecular weight PEP (Shamrock, Newark, N.J.; 12.5 micron particles, 2.8 g) and 13 mL of chromic acid solution were heated at 75° C. for 30 minutes. The hot suspension was filtered on a coarse sintered glass funnel. The product was then washed with water, 0.1M NaOH solution, water, 0.1M HCl, water until neutral, then methanol and dried. The total dried product was suspended in 1:1 acetonitrile/1,13 diamino-3,6,9-trioxatridecane (10 mL), BOP (3×0.5 g) added at 1 hour intervals and the reaction swirled overnight. The suspension was filtered, washed with DMF, dioxan/ water (1:1, 2×); then treated with sodium borohydride (0.2 g) in 10 mL 1:1 dioxan/water for 1 hour on the sintered funnel. The suspension was filtered, and washed with water. These washes were isolated and subsequently carefully treated to decompose excess borohydride. The particles were then washed 0.1M HCl (2×), 0.1M NaOH (2×), water (until neutral), methanol (3×) and dried to give aminofunctionalized product (2.5 g) which had a loading of 13.5 µmol/g. This was suspended in acetonitrile, 10 mL, and pyridine (1 mL) and palmitoyl chloride (1 mL) added. The reaction was gently stirred overnight, then filtered, and the particles washed with DMF, water and methanol, and dried.

EXAMPLE 7

Use for DNA synthesis

90 Micron PEP (80 g) was chemically invected and aminofunctionalised as described in Example 4 above to give a CPE loading 80 μmol/g. A sample (20 g) was stirred gently in acetonitrile, and an activated solution of Fmoc-Ile-OH (0.177 g, 0.5 mmol), BOP (0.25 g) and HOBt (0.06 g) in 2 mL 0.3M NMM in acetonitrile added, washed in with further acetonitrile. The suspension was gently stirred overnight, filtered, washed with DMF, and acetylated on the sintered funnel with 100 mL of 0.3M acetic anhydride + HOBt in DMF for 30 minutes. The suspension was filtered, washed with DMF (×5), then treated with 30% Piperidine in DMF (100 mL) for 15 minutes. The suspension was refiltered, washed with DMF (×5), and methanol (×3) and dried. The total product was suspended in acetonitrile (40 mL), swirled gently and an activated solution of DMT-T-hemisuccinate (0.66 g), BOP (0.53 g) and HOBt (0.13 g) in 0.3M NMM in acetonitrile (5 mL) added, washed in with more acetonitrile. The suspension was reacted overnight, then washed with DMF, and THF, and capped for 10 minutes with a mixture of acetic anhydride/lutidine, and N-methylimidazole in THF prepared by mixing together 50 mL aliquots of commercial Beckman synthesis reagents CAP A and CAP B. The support was washed with DMF (3×), Methanol (3×), and dried to give a loading of 28 μmol/g. This material in flow through column reactors and commercial DNA synthesizers run on scales from 0.2 μmol to 200 μmol performed as efficiently as did CPG in control syntheses (judged by DMT colors during synthesis, and reverse phase HPLC analysis of the products).

EXAMPLE 8

Use for soluble and immobilized peptide synthesis

A 55 micron PEP was amino functionalized as described in Example 4, giving, after the chemical invection process, a loading of 110 μmol/g. A portion (8 g) was treated overnight with Rink Amide Linker (0.81 g, 1.5 mmol, NovaBiochem), BOP (0.70 g, 1.6 mmol) and anhydrous HOBt (0.20 g, 1.6 mmol) in acetonitrile (8 mL) and 0.3M N-methylmorpholine in acetonitrile (8 mL). After swirling overnight the support was filtered washed with DMF, methanol and dried (8.33 g, ninhydrin negative). Both amino and Rink linked supports (0.5 g each) were packed in Biosearch Excell column reactors and treated to cycles of successive amino acid incorporation: i) wash DMF (3×), ii) Fmoc removal, 30% Piperidine in DMF (1 min, 15 min), iii) wash DMF (3×), acetonitrile (2×); iv) Couple Fmoc-Aa-OH [Gly, 0.30 g; Tyr(tBu), 0.46 g; Ala, 0.31 g; Lys(Boc), 0.47 g; Gly 0.30 g; Tyr(tBu), 0.46 g each in the presence of BOP, 0.45 g, HOBt 0.12 g and 4 mL 0.3M NMM in acetonitrile, coupled between 1 and 2 hours]. The final Fmoc group was removed, and the supports washed with DMF, methanol and dried. The Rink linked peptide support was cleaved and deprotected for 2×10 minutes with 95% TFA/5% water, then the pooled eluants left for 1.5 hours, concentrated under nitrogen and the product precipitated by the addition of anhydrous ether. It was filtered, washed with ether and dried to give the peptide YGKAYG-amide (30 mg, >90% pure by HPLC assay). The immobilized peptide was deprotected by 2 treatments with 95% TFA (10 min, 1 h 20 min), washed with methanol and dried.

EXAMPLE 9

Use in particle based library application

A. Sixteen aliquots (each 1 g) of 90 micron CPE, loading 80 μmol/g after amino-substitution, were placed in scintillation vials and each coupled with one of Fmoc-D-Ala-OH, 0.31 g; Fmoc-L-Ala-OH, 0.31 g; Fmoc-L-Asp(OtBu)-OH, 0.41 g; Fmoc-L-Arg (Pmc) -OH, 0.66 g; Fmoc-L-Glu (OtBu) -OH, 0.43 g; Fmoc-L-Gln (Trt) -OH, 0.61 g; Fmoc-Gly-OH, 0.30 g; Fmoc-L-His (Trt) -OH, 0.62 g; Fmoc-L-Lys (Boc) -OH, 0.47 g, Fmoc-L-Nle-OH, 0.35 g, Fmoc-L-Phe-OH, 0.39 g; Fmoc-L-Trp (Boc) -OH, 0.55 g; Fmoc-L-Pro-OH, 0.34 g; Fmoc-L-Ser (tBu) -OH, 0.39 g; Fmoc-L-Tyr (tBu) OH, 0.46 g; Fmoc-L-Val-OH, 0.34 g each in the presence of BOP, 0.45 g and HOBt, 0.12 g activated with 4 mL of 0.3M NMM for 2 hours. The particles were mixed, deprotected with 30% Piperidine in DMF (1 min, 15 min), washed with DMF and acetonitrile, suspended in acetonitrile and proportioned by syringe into a further 16 scintillation vials. This process was continued for 6 addition cycles, the last Fmoc groups removed, deprotection with TFA/methanol/triisopropylsilane (96:2:2) performed for 10 min, then 1 h 20 min), washed with methanol and dried. This particle based library has $16.77 \times 10^6$ components.

B. Amino-functionalized 90 micron CPE was loaded with biotin. Additionally, the CPE bound peptide HPQFSG was assembled exactly as described in Example 8. Aliquots (1 mg) of these 2 samples were separately mixed with 1 g aminofunctionalized CPE and treated with ELF substrate, and strepatvidin-alkaline phosphatase conjugate under conditions described by the reagent kit manufacturers (Molecular Probes). The incubated suspensions were filtered, washed quickly twice with assay buffer, then irradiated under long wave length u.v. Vivid fluorescence was observed on ca. 1 particle in 1 thousand. This experiment was repeated with unspiked aminofunctionalized beads (no detection), and with the library prepared in A, which showed numerous positive beads.

EXAMPLE 10

Use in enzyme immobilization

A 90 micron aminofunctionalized CPE (loading 60 μmol/g, 1 g) in acetonitrile/pyridine (1:1, 5 mL), was gently swirled overnight with succinic anhydride (0.3 g). The particles were filtered, washed with DMF, then acetonitrile (ninhydrin test, negative). They were resuspended in acetonitrile (1 mL), TSTU reagent (Advanced ChemTech, 0.1g) added, followed by 0.3M N-methylmorpholine in acetonitrile (1 mL). The suspension was gently swirled over night, then filtered, washed with acetonitrile and dried.

Trypsin (5.9 mg) was added to a suspension of the succinimide activated CPE (100 mg) in 0.5 mL phosphate buffer pH 7.6 and acetonitrile (100 μL), and the suspension gently swirled overnight. The particles were filtered, washed repeatedly with water containing 15% acetonitrile, then stored damp at 0° C. For use, the entire lot was washed repeatedly with assay buffer (0.16 g Tris.HCl, 0.13 g Tris, 35 mg of calcium acetate in 20 mL water, pH 8). Approximately a third of the immobilized enzyme was removed and 1 mg of YGKAYG-amide [viii above] in 1:1 acetonitrile/water (200 μL) added. After 5 minute digestion HPLC assay (Beckman Ultrasphere XL 3 micron column, buffer A 0.05% TFA in water, buffer B 0.05% TFA in acetonitrile, flow 1.3 mL/min., detn at 230 nm, gradient to 100% B over 30 minutes) showed total hydrolysis of peptide (elution 6.1 minutes) forming 2 equal new peptides, eluting at 4.1 min (AYG-amide) and 4.5 min (YGK)

EXAMPLE 11

Enzymatic Modification of CPO bound Molecules

The CPE immobilized peptide YGKAYG (100 mg) was suspended in Tris assay buffer (500 µl), and treated with trypsin (200 µg) in 400 µl buffer. HPLC assay (details given above, x) showed rapid liberation of YGK into solution complete in 30 minutes.

Boc-Trp-Gly-CPE was prepared as usual, and an aliquot (0.5 g) suspended in 0.1M ammonium bicarbonate pH 7.5 (500 µl) and acetonitrile (100 µl). Chymotrypsin (5 mg) was added, and samples (500 µl) of the suspension removed at various times, the treated particles washed repeatedly with water, then methanol and dried. Samples were derivatized with DMT-T-succinate as described under nucleotide synthesis. Loading determination, by release of DMT cation with 3% DCA in methylene chloride, as well as by quantitative ninhydrin assay directly on the trypsinized samples, showed controlled Trp-Gly cleavage with a $t_{1/2}$ of 1 hour, and overnight cleavage liberating 50–70% of total amino-functionalization of the amino-CPE used. This procedure represents a practical method for selecting only highly accessible sites on CPE surfaces, as well as providing a method to construct 2 different molecules on the same physical particle.

EXAMPLE 12

Use with Orthogonally Cleaved Linkers in Organic Synthesis Applications

A. Preparation of 4-hydroxymethylbenzoyl CPE (Hmb-CPE).

Hydroxymethylbenzoic acid (0.3 g, 2 mmol) and anhydrous 1-hydroxybenzotriazole (0.27 g, 2 mmol) in 01:1 methylene chloride/DMF (5 mL) were treated with diisopropylcarbodiimide (0.32 ml, 2 mmol), and the mixture added to 90 micron amino-functionalised CPE (1 g, 60 µmol). The suspension was gently stirred overnight, then filtered, and the CPE washed with DMF and methylene chloride.

B. Michael Reaction.

4-Methoxycinnamic acid (0.29 g, 1.66 mmol) in 1:1 methylene chloride/DMF (5 mL) was treated with diisopropylcarbodiimide (0.27 ml, 1.66 mmol) and dimethylaminopyridine (0.20 g, 1.66 mmol). The mixture was immediately added to Hmb-CPE (1 g) prepared above, and mixed gently overnight. The CPE was filtered, washed extensively with DMF, and methanol, and dried. A portion of this support was treated in a tube with anhydrous tetrapropylammonium hydroxide (100 mg) in nitromethanol (1.5 mL), the tube was tightly sealed and heated at 70° C. for 6 hours. Simultaneously, 4-methoxycinnamic acid methyl ester (50 mg) was treated exactly equivalently. After 6 hours, the CPE supported reaction were washed with DMF, and methanol, and the product dried. The solution reaction was diluted with methylene chloride, washed with 0.5M HCl, sat. NaHCO$_3$, dried over MgSO$_4$ and the solution evaporated. The CPE and solution products were either dissolved or suspended in methanol (0.5 mL), and treated with 2M NaOH (0.5 mL). After 1 hour the solution reaction was terminated by acidification (1.5 mL, 1M HCl), the product extracted into methylene chloride 3 mL, washed with water, dried over MgSO$_4$ and evaporated. The CPE cleavage reaction was filtered, and the filtrate treated exactly as for the solution reaction. The yield of the product, R, S 3-nitro-2- (4'-methoxyphenyl) -butyric acid (an analog of a key intermediate in the synthesis of the hypnotic and muscle relaxant, baclofen), as assayed by thin layer chromatography (GF$_{254}$ toluene/dioxan/acetic acid 25:4:1):-CPE product yield 90% (containing 10% unreacted methoxycinnamic acid); solution yield 95% (containing 1–2% methoxycinnamic acid). This, and other comparisons, show that CPE supported organic reactions occur at only marginally slower rates than do their solution counterparts.

EXAMPLE 13

Preparation of Immobilized Chemical Reagents

4-Pyridylacetic acid hydrochloride (0.85 g, 5 mmol) was suspended in DMF (10 mL), and BOP (2.25 g, 5 mmol), HOBt (0.68 g, 5 mmol) and N-methyl morpholine (1.9 mL, 15.8 mmol) added. The mixture was added to aminofunctionalized 90 micron CPE (prepared as in Example 4 above, 5 g, 0.4 mmol) in DMF (10 mL) and swirled gently overnight. The suspension was filtered, and the particles washed with DMF and THF. They were then treated with 50 mL of Beckman Cap A reagent and 50 mL of Beckman Cap B reagent for 30 minutes on the scintered funnel. The suspension was then filtered, washed with DMF, 10% N-methyl morpholine in DMF (3×100 mL), DMF, acetonitrile and dried.

A. CPE Bound Oxidising Reagent.

Chromium trioxide (1 g) was added to 4 mL water and 1 mL c. hydrochloric acid, then 1 g of pyridyl-CPE (above) added. The reaction was swirled gently for 1 hour, then the suspension filtered and the particles washed with water until the eluant was colorless. The bright orange particles were dried in vacuo.

B. CPE Bound Reducing Reagent

Pyridyl-CPE (2 g) was suspended in THF (10 mL) under nitrogen and treated with 1M borane in THF (2 mL). The reaction was gently agitated for 1 hour, then filtered, and the particles washed with THF. These were dried in vacuo, and stored under nitrogen.

EXAMPLE 14

Use of CPO's for Chromatographic Separations.

Sample CPO's were slurry packed in acetonitrile at a flow rate of 4 mL minute in 4 mm×7.5 cm Upchurch Scientific Omega columns. For reverse phase protein separations the system employed buffer A, 0.05% TFA in water, buffer B, 0.05% TFA in acetonitile, flow 1.3 mL/min, detection at 230 nm, gradient linear from 0%B to 100%B over 30 minutes. For reverse phase nucleotide separations a similar system was used with buffer A 0.1M ammonium acetate, buffer B acetonitrile. For anion exchange separations buffer A was 0.05M Tris pH 7.5 containing 20% acetonitrile, buffer B was buffer A modified by the addition of 1M potassium chloride. Palmitoylated and C-18 functionalized CPO's functioned efficiently to provide reverse phase separation of synthetic DNA, and 5' functionalized DNA. For protein separations excellent results, including base line resolution of lysozyme, ribonuclease and bovine serum albumin (Fraction V) were obtained with hydroxylated CPO's (derived by LiAlH$_4$ reduction of oxidized CPO's as described in Example 3a above). Ion-exchange separation of failure sequences in synthetic DNA samples was obtained with tertiary amine functionalized CPO's, (Example 3c). A principle merit of CPO's in this application is the very low back-pressure provided, which permits very large scale separations to be envisioned.

We claim:

1. Polyethylene or polypropylene particles modified by oxidation to have a chemically reactive irregular surface and open channels that extend below the surface and up to essentially the length of the radius of the particles to provide increased surface area and decreased density, said oxidation carried out by a process comprising suspending solid polyethylene or polypropylene particles having a particle size of about 1 to about 2,000 microns in an oxidizing solution containing trifluoroacetic acid or trifluoromethane sulfonic acid, chromium trioxide and sulfuric acid, and maintaining the particles in the solution for a time and at a temperature sufficient for oxidation of the particles to provide said irregular surface, said open channels that extend below the surface and up to essentially the length of the radius and said increased surface area and decreased density, and the size of said particles being essentially unchanged by said oxidation.

2. The particles according to claim 1 where said oxidation and/or an additional reaction has provided said particles with pendant functional groups selected from the group consisting of carboxyl, keto, hydroxyl, aldehyde, primary amino, secondary amino, tertiary amino, quaternary amino, phosphoric and sulfonate.

3. The particles according to claim 2 wherein the pendant functional groups have attached organic reagents capable of performing a chemical reaction on a molecule in solution.

4. The particles according to claim 2 wherein a protein is immobilized on the particles by attachment to the pendant functional groups.

5. The particles according to claim 2 wherein an enzyme is immobilized on the particles by attachment to the pendant functional groups.

6. The particles according to claim 2 wherein viable whole cells are immobilized on the particles.

7. The particles according to claim 2 wherein the pendant functional groups have attached hydrocarbon functional groups of 3 to 30 carbon atoms for reverse phase liquid chromatography.

8. The particles according to claim 2 wherein the pendent functional groups have attached aromatic functional groups of 1 to 3 rings for reverse phase liquid chromatography.

9. The particles according to claim 2 wherein the pendant functional groups are selected from the group consisting of primary amino, secondary amino, tertiary amino, quaternary amino, carboxyl, phosphoric and sulfonate for ion exchange liquid chromatography.

10. The particles according to claim 2 wherein the pendant functional groups have attached chemically or enzymatically synthesized oligonucleotides in protected or free form.

11. The particles according to claim 2 wherein the pendant functional groups have attached chemically or enzymatically synthesized oligosaccharides in protected or free form.

12. The particles according to claim 2 wherein the pendant functional groups have attached chemically or enzymatically synthesized peptides or proteins in protected or free form.

13. The particles according to claim 2 wherein the pendant functional groups have attached organic molecules coupled by a single attachment step or by successive attachment steps.

14. The particles according to claim 1 wherein individual particles are physically joined into larger conglomerates.

15. The particles according to claim 2 wherein the pendant functional groups are separated from the surface of the particles by linear hydrocarbon, branched hydrocarbon, polyethylene glycol or polyamine spacer arms.

16. A process for chemically or enzymatically mediated oligonucleotide synthesis wherein the particles of claim 2 are used as a support.

17. A process for chemically or enzymatically mediated peptide synthesis wherein the particles of claim 2 are used as a support.

18. A process for chemically or enzymatically mediated oligosaccharide synthesis wherein the particles of claim 2 are used as a support.

19. A process for chemical assembly of organic molecules wherein the particles of claim 2 are used as a support.

\* \* \* \* \*

UNITED STATES PATENT AND TRADEMARK OFFICE
CERTIFICATE OF CORRECTION

PATENT NO. : 5,679,539
DATED : October 21, 1997
INVENTOR(S) : Derek Hudson and Ronald M. Cook et al.

It is certified that error appears in the above-identified patent and that said Letters Patent is hereby corrected as shown below:

<u>Column 1,</u>
Line 5, before "FIELD OF INVENTION" please insert a new paragraph:
-- STATEMENT AS TO RIGHTS TO INVENTIONS MADE UNDER
FEDERALLY SPONSORED RESEARCH OR DEVELOPMENT The work disclosed herein was partially supported by a grant by The Government of the United States, as represented by the Secretary of the Department of Health and Human Services (Contract Nos. IR44GM50593 and IR44GM55013). --

Signed and Sealed this

Twenty-sixth Day of March, 2002

*Attest:*

*Attesting Officer*

JAMES E. ROGAN
*Director of the United States Patent and Trademark Office*